US012662455B2

(12) United States Patent
Norman et al.

(10) Patent No.: US 12,662,455 B2
(45) Date of Patent: *Jun. 23, 2026

(54) TETRAHYDROBENZO-QUINOLINE SULFONAMIDE DERIVATIVES USEFUL AS IgE MODULATORS

(71) Applicant: UCB Biopharma SRL, Brussels (BE)

(72) Inventors: Timothy John Norman, Slough (GB); Selvaratnam Suganthan, Abingdon (GB); Jag Paul Heer, Slough (GB); Zeshan Yousuf, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 847 days.

This patent is subject to a terminal disclaimer.

(21) Appl. No.: 17/786,309

(22) PCT Filed: Dec. 22, 2020

(86) PCT No.: PCT/EP2020/087688

§ 371 (c)(1),
(2) Date: Jun. 16, 2022

(87) PCT Pub. No.: WO2021/130260

PCT Pub. Date: Jul. 1, 2021

(65) Prior Publication Data

US 2023/0050670 A1 Feb. 16, 2023

(30) Foreign Application Priority Data

Dec. 23, 2019 (GB) ...................................... 1919214

(51) Int. Cl.
*C07D 221/06* (2006.01)
*C07D 413/14* (2006.01)

(52) U.S. Cl.
CPC ......... *C07D 221/06* (2013.01); *C07D 413/14* (2013.01)

(58) Field of Classification Search
CPC .. C07D 221/06; C07D 413/14; C07D 401/04; C07D 401/14; C07D 401/12; A61P 11/00
See application file for complete search history.

(56) References Cited

U.S. PATENT DOCUMENTS

| | | | | |
|---|---|---|---|---|
| 4,857,301 | A * | 8/1989 | Czarniecki | C07D 401/12 546/139 |
| 5,340,811 | A | 8/1994 | Kajihara et al. | |
| 5,962,634 | A | 10/1999 | Jameson et al. | |
| 12,410,161 | B2 | 9/2025 | Norman et al. | |
| 2007/0027184 | A1 | 2/2007 | Malecha et al. | |
| 2007/0179127 | A1* | 8/2007 | Yamada | A61P 25/16 514/307 |
| 2009/0156642 | A1 | 6/2009 | Nishida et al. | |
| 2023/0192646 | A1* | 6/2023 | Norman | C07D 401/12 514/252.03 |
| 2023/0303517 | A1* | 9/2023 | Norman | C07D 401/14 |
| 2024/0092773 | A1* | 3/2024 | Norman | C07D 413/14 |

FOREIGN PATENT DOCUMENTS

| | | | |
|---|---|---|---|
| CN | 1050183 | A | 3/1991 |
| EP | 0418071 | A2 | 3/1991 |
| EP | 0 419 676 | | 4/1991 |
| GB | 2270689 | | 3/1994 |
| JP | 2007 099676 | X | 4/2007 |
| JP | 2017-501215 | | 1/2017 |
| WO | 1996/01643 | | 1/1996 |
| WO | 199828293 | A1 | 7/1998 |
| WO | WO 2004/058709 | | 7/2004 |
| WO | 2008059368 | A2 | 5/2008 |
| WO | WO 2008/129276 | | 10/2008 |
| WO | 2009041705 | A2 | 4/2009 |
| WO | 2015080707 | A1 | 6/2015 |

(Continued)

OTHER PUBLICATIONS

Gomez, Gregorio. "Current Strategies to Inhibit High Affinity FcεRI-Mediated Signaling for the Treatment of Allergic Disease." Frontiers in Immunology, vol. 10, Feb. 2019. Frontiers, https://doi.org/10.3389/fimmu.2019.00175. (Year: 2019).*

Smith, Lucy D., et al. "Development of Small Molecules to Target the Ige:FcεRi Protein—Protein Interaction in Allergies." Future Medicinal Chemistry, vol. 5, No. 12, Aug. 2013, pp. 1423-1435. DOI.org (Crossref), https://doi.org/10.4155/fmc.13.112. (Year: 2013).*

English Translation of The office action issued in by the Japanese Patent Office for JP Patent Application No. 2022-538776 dated Oct. 22, 2024, 2 pages.

Sarkar Tarun K. et al: "A Sequential Pummerer-Diels-Alder Route for the generation and Trapping of Furo [3,4-c]pyridines: Synthesis of Heterocyclic Analogues of 1-Arylnaphthalene Lignans", Journal of Organic Chemistry, vol. 68, No. 18, Sep. 1, 2003, pp. 6919-6927.

(Continued)

*Primary Examiner* — Clinton A Brooks
*Assistant Examiner* — Kyle Nottingham
(74) *Attorney, Agent, or Firm* — McDonnell Boehnen Hulbert & Berghoff LLP

(57) ABSTRACT

The present invention relates to tetrahydrobenzo-isoquinoline sulfonamide derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

(I)

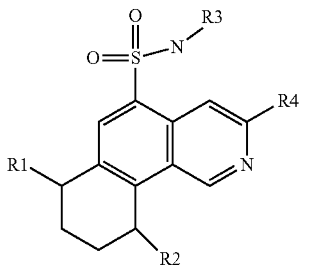

15 Claims, No Drawings

(56) References Cited

FOREIGN PATENT DOCUMENTS

| | | |
|---|---|---|
| WO | 2019/243550 | 12/2019 |
| WO | 2021/130255 | 7/2021 |
| WO | 2021/130259 | 7/2021 |
| WO | 2021/130262 | 7/2021 |

OTHER PUBLICATIONS

International Search Report dated Feb. 25, 2021 for International Application No. PCT/EP2020/087688, 3 pages.

Parisi, Gluseppe Fablo et al. "Omalizumab treatment in a 12 year-old girl with chronic spontaneous urticaria" The Journal of Dermatological Treatment (2018) vol. 29, pp. 10-11.

Hay, Michael P. et al. "Tricyclic 1-18 [1,2,4]triazine 1,4-dioxides as hypoxia selective cytotoxins" Journal of Medicinal Chemistry (2008) vol. 51(21), pp. 6853-6865.

Kitagaki, Shinji et al. "Intermolecular [4 + 2] Cycloaddition of o -Quinodimethanes Derived from Ene-Bis (sulfinylallenes)" Journal of Organic Chemistry (2006) vol. 71(18), pp. 6908-6914.

Jun Kohno et al. "Production, Isolation and Biological Properties of TMC-120A, B and C, Novel Inhibitors of Eosinophil Survival from Aspergillus ustus TC 1118. Journal of Antibiotics" (1999) vol. 52(10), pp. 913-916.

* cited by examiner

TETRAHYDROBENZO-QUINOLINE SULFONAMIDE DERIVATIVES USEFUL AS IgE MODULATORS

CROSS-REFERENCE TO RELATED APPLICATIONS

This application is a U.S. national phase of International Application No. PCT/EP2020/087688, filed Dec. 22, 2020, which claims priority from Great Britain Application No. 1919214.5, filed Dec. 23, 2019, the disclosure of each of which is hereby incorporated by reference in its entirety.

TECHNICAL FIELD

The present invention relates to tetrahydrobenzo-isoquinoline sulfonamide derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

BACKGROUND OF THE INVENTION

IgE (immunoglobulin E) is a member of the immunoglobulin family and mediates allergic responses such as asthma, food allergies, type 1 hypersensitivity and the familiar sinus inflammation.

IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII). Upon exposure of a mammal to an allergen, B-cells are clonally amplified which synthesize IgE that binds the allergen. This IgE in turn is released into the circulation by the B-cells where it is bound by B-cells (through FcεRII) and by mast cells and basophils through the so-called high affinity receptor (FcεRI) found on the surface of the mast cells and basophils. Such mast cells and basophils are thereby sensitized for allergen. The next exposure to the allergen cross-links the FcεRI on these cells and thus activate their release of histamine and other factors which are responsible for clinical hypersensitivity and anaphylaxis.

Currently, allergic diseases, urticaria, and asthma are usually treated with one or more of the following drugs: (1) antihistamines and antileukotrienes which antagonize the inflammatory mediators histamine and leukotrienes, (2) local or systemic (oral or injectable) corticosteroids or immunosuppressants which suppress a broad spectrum of inflammatory mechanisms, (3) short or long-acting bronchodilators which relax smooth muscle of constricted airway in asthma, or (4) mast cell stabilizers which inhibit the degranulation of mast cells that is normally triggered by IgE-binding at FcεRI, (5) biologicals which prevent the binding of IgE at FcεRI. There has been also attempts to use peptides that modulate IgE binding to FcεRI. As an example, WO96/01643 describes peptides that consist of 4-50 amino to treat immediate allergic responses.

However, there is still a need to identify compounds which have therapeutic utility in the treatment or prevention of disorders caused by IgE, particularly disorders caused by the interaction of IgE with the FcεRI receptor.

SUMMARY OF THE INVENTION

It has been found that compounds of formula (I) and their pharmaceutically acceptable salts can be used for this purpose.

DETAILED DESCRIPTION

The present invention provides compounds of formula (I) and pharmaceutically acceptable salts thereof:

(I)

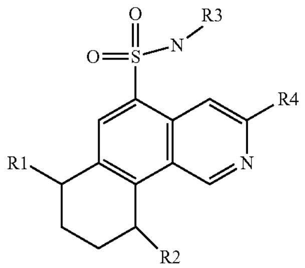

R1, R2 represents independently from each other a group chosen amongst:

Hydrogen; or NHC(O)NH—C1-6-alkyl; or $NHSO_2$-C1-6-alkyl; or NHC(O)NH-heteroaryl optionally substituted with one or more $R1_a$; or heteroaryl optionally substituted with one or more group chosen amongst amino; C1-6-alkyl; C(O)O—C1-6-alkyl; nitrile; heteroaryl optionally substituted with one or more $R1_a$; NH—C1-6-alkyl; NH—C1-6-heterocycloalkyl; NH—C3-9-cycloalkyl; NH-heteroaryl optionally substituted with one or more $R1_a$; or NH-heteroaryl optionally substituted with one or more group chosen amongst; C1-6-alkyl; C1-6-hydroxyalkyl; C3-9-hydroxyheterocycloalkyl;

heteroaryl optionally substituted with one or more $R1_a$; or NHC(O)—C1-6-alkyl; or NHC(O)-heteroaryl optionally substituted with one or more $R1_a$ $R1_a$ represents a group chosen amongst:

Halogen; nitrile; C1-6-alkyl; C1-6-haloalkyl; C1-6-alkoxy; C1-6-haloalkoxy; C(O)O—C1-6-alkyl; C(O)OH;

R3 represents a group chosen amongst:

C1-6-alkyl optionally substituted with one or more group chosen amongst $R3^a$;

C1-3-alkanediyl-C3-6-cycloalkyl optionally substituted with one or more $R3^a$;

C1-3-alkanediyl-C3-6-heterocycloalkyl optionally substituted with one or more $R3^a$;

C3-6-heterocycloalkyl optionally substituted with one or more $R3^a$;

C3-6-cycloalkyl optionally substituted with one or more $R3^a$;

$R3^a$ represents a group chosen amongst hydrogen Halogen, C1-2-alkyl; hydroxy; C1-2-alkoxy R4 represents a group chosen amongst:

C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group;

$R4^a$ represents a group chosen amongst hydroxy; Halogen; C1-2-alkyl.

The term "pharmaceutically acceptable salt" according to the invention embraces salts of the compounds of formula (I) with a pharmaceutically acceptable acid or base, in particular an acid addition salt. The acid addition salt form of a compound of formula (I) that occurs in its free form as a base can be obtained by treating the free base with an appropriate acid such as an inorganic acid, for example, a hydrohalic acid such as hydrochloric acid or hydrobromic acid, sulfuric acid, nitric acid, phosphoric acid and the like; or an organic acid, such as, for example, acetic acid, trifluoroacetic acid, oxalic acid, hydroxyacetic acid, propanoic acid, lactic acid, pyruvic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and the like.

The invention also relates to all stereoisomeric forms such as enantiomeric and diastereoisomeric forms of the compounds of formula (I) or mixtures thereof (including all possible mixtures of stereoisomers such as racemates). With respect to the present invention reference to a compound or compounds is intended to encompass that compound in each of its possible isomeric forms and mixtures thereof, unless the particular isomeric form is referred to specifically.

Some of the compounds of formula (I) may also exist in tautomeric forms. Such forms although not explicitly indicated in the above formula are intended to be included within the scope of the present invention.

It is to be understood that each individual atom present in formula (I), or in formulae depicted herein, may in fact be present in the form of any of its naturally occurring isotopes, with the most abundant isotope(s) being preferred. Thus, by way of example, each individual hydrogen atom present in formula (I), or in the formulae depicted herein, may be present as a 1H, 2H (deuterium) or 3H (tritium) atom, preferably 1H. Similarly, by way of example, each individual carbon atom present in formula (I), or in the formulae depicted herein, may be present as a 12C, 13C or 14C atom, preferably 12C.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The present invention also includes within its scope prodrug of the compounds of formula (I) above. The term "prodrug" means a compound metabolised in vivo to a compound of the invention or its salt. A prodrug may be identified by administering the prodrug to a mammal, such as rat, mouse, monkey or man, and identifying the compound or its salt, for example in blood or urine.

In the frame of the present invention:

Ct-z represents a carbon chain which may have from t to z carbon atoms, for example a C1-7 carbon chain which may have from 1 to 7 carbon atoms;

Alkyl is a saturated, linear or branched aliphatic group; for example, a C1-6-alkyl group represents a carbon chain of 1 to 6 carbon atoms, linear or branched, for example a methyl, ethyl, propyl, isopropyl, butyl, isobutyl, tertbutyl, pentyl, hexyl. Alkyl encompass deuterated groups, where one or more hydrogen atoms are replaced with deuterium atom $^2H$.

Alkanediyl is a divalent linear or branched saturated hydrocarbon group of general formula $C_nH_{2n}$, such as $—CH_2—CH_2—$;

Alkylamino refers to one or more alkyl groups substituted on an amino radical. As examples of alkylamino one can mention methylamino; ethylamino; tertbutylamino; dimethylamino; hydroxy is a —OH group;

hydroxyalkyl is an alkyl group of which one or more hydrogen atom has been substituted with a hydroxy group;

haloalkyl is an alkyl group of which one or more hydrogen atom has been substituted with a halogen atom;

alkoxy, —O-alkyl group;

haloalkoxy is an alkoxy group of which one or more hydrogen atom has been substituted with a halogen atom;

halogen atom, a fluorine, chlorine, bromine or iodine atom;

cycloalkyl refers to a mono or bicyclic aliphatic group that may comprise a double bond without being aromatic and comprising between 3 and 14 atoms, preferably 3 to 9 atoms in the group. As an example of cycloalkyl one can mention cyclopropyl; cyclobutyl; cyclobutenyl; cyclopentyl; cyclohexyl; spiro-undecanyl; spiro[2.2]pentanyl heterocycloalkyl refers to a mono or bicyclic saturated group comprising between 3 and 14 atoms, preferably between 3 and 10 atoms in the group that may comprise a double bond without being aromatic and wherein one or more carbon atom is replaced with an atom chosen amongst nitrogen; oxygen; sulfur. As an example of heterocycloalkyl one can mention aziridinyl; pyrrolidinyl; piperidyl; oxetane; oxa-spiro-undecanyl;

hydroxyheterocycloalkyl is an heterocycloalkyl group of which one or more hydrogen atom has been substituted with a hydroxy group;

Heteroaryl refers to a mono- or bicyclic group comprising from 5 to 14, preferably 5 to 10 atoms wherein at least one ring in the group is aromatic and wherein at least one atom in the group is chosen amongst nitrogen; oxygen; sulfur. As examples of a heteroarylgroup one can mention triazolyl; furanyl; pyrrolyl; chromanyl; isoquinolinyl.

According to an embodiment, compounds of the invention are chosen amongst compounds of formula (I) wherein:

when R1 is different than hydrogen, R2 is hydrogen;

when R2 is different than hydrogen, R1 is hydrogen;

other substituents are as herein defined above and below.

According to an embodiment, compounds of the invention are chosen amongst compounds of formula (I) wherein:

R3 represents a group chosen amongst:

C1-6-alkyl optionally substituted with one or more group chosen amongst $R3^a$;

C1-3-alkanediyl-C3-6-cycloalkyl optionally substituted with one or more $R3^a$;

C1-3-alkanediyl-C3-6-heterocycloalkyl optionally substituted with one or more $R3^a$;

C3-6-heterocycloalkyl optionally substituted with one or more $R3^a$;

C3-6-cycloalkyl optionally substituted with one or more $R3^a$;

$R3^a$ represents a group chosen amongst hydrogen Halogen, C1-2-alkyl; hydroxy; C1-2-alkoxy; other substituents are as herein defined above and below.

According to an embodiment, compounds of the invention are chosen amongst compounds of formula (I) wherein:

R4 represents a group chosen amongst:

C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group;

$R4^a$ represents a group chosen amongst hydroxy; Halogen; C1-2-alkyl;

other substituents are as herein defined above and below.

According to an embodiment, compounds of the invention are chosen amongst compounds of formula (I) wherein:

R4 represents cyclopropyl;

other substituents are as herein defined above and below.

Another embodiment of the present invention concerns a pharmaceutical composition comprising a detectable amount of a compound of formula (I) or a pharmaceutically acceptable salt, solvate or co-crystal thereof in combination with a pharmaceutically acceptable diluent or carrier.

In yet another embodiment, the present invention concerns a compound of formula (I), a pharmaceutically acceptable salt, solvate or co-crystal thereof for use as a medicament, in particular for use in a method for the treatment or prevention of disorders caused by IgE, including allergy, type 1 hypersensitivity, familiar sinus inflammation, urticaria or related conditions, such as airway constriction in asthma, local inflammation in eczema, increased mucus secretion in allergic rhinitis, or increased vascular permeability.

In a further embodiment, the present invention concerns a method for the treatment or prevention of allergy, type 1 hypersensitivity, familiar sinus inflammation, urticaria or related conditions, which comprises the administration of a compound of formula (I) in a therapeutically effective amount.

According to an embodiment, compounds of the invention are chosen amongst:

3-cyclopropyl-N-(2-methylpropyl)-7,8,9,10-tetrahydrobenzo[h]isoquinoline-5-sulfonamide;

1-[3-cyclopropyl-5-(2-methylpropylsulfamoyl)-7,8,9,10-tetrahydrobenzo[h]isoquinolin-7-yl]-3-ethylurea;

1-[3-cyclopropyl-5-(2-methylpropylsulfamoyl)-7,8,9,10-tetrahydrobenzo[h]isoquinolin-10-yl]-3-ethylurea;

3-cyclopropyl-7-(methanesulfonamido)-N-(2-methylpropyl)-7,8,9,10-tetrahydrobenzo[h]isoquinoline-5-sulfonamide;

3-cyclopropyl-10-(methanesulfonamido)-N-(2-methylpropyl)-7,8,9,10-tetrahydrobenzo[h]isoquinoline-5-sulfonamide;

3-cyclopropyl-N-(2-fluoro-2-methylpropyl)-7-[[6-(2-methyltetrazol-5-yl)pyridin-3-yl]amino]-7,8,9,10-tetrahydrobenzo[h]isoquinoline-5-sulfonamide;

3-cyclopropyl-7-[3-[(2,5-dimethylpyrazol-3-yl)amino]-1,2,4-triazol-4-yl]-N-(2-fluoro-2-methylpropyl)-7,8,9,10-tetrahydrobenzo[h]isoquinoline-5-sulfonamide;

3-cyclopropyl-N-(2-fluoro-2-methylpropyl)-10-[[6-(2-methyltetrazol-5-yl)pyridin-3-yl]amino]-7,8,9,10-tetrahydrobenzo[h]isoquinoline-5-sulfonamide;

ethyl 5-amino-1-[3-cyclopropyl-5-[(2-fluoro-2-methylpropyl)sulfamoyl]-7,8,9,10-tetrahydrobenzo[h]isoquinolin-7-yl]imidazole-4-carboxylate;

3-cyclopropyl-N-(2-fluoro-2-methylpropyl)-7-[[5-(3-methyl-1,2,4-oxadiazol-5-yl)pyridin-3-yl]amino]-7,8,9,10-tetrahydrobenzo[h]isoquinoline-5-sulfonamide;

1-[3-cyclopropyl-5-[(2-fluoro-2-methylpropyl)sulfamoyl]-7,8,9,10-tetrahydrobenzo[h]isoquinolin-7-yl]-3-(2,5-dimethylpyrazol-3-yl) urea;

ethyl 1-[3-cyclopropyl-5-[(2-fluoro-2-methylpropyl)sulfamoyl]-7,8,9,10-tetrahydrobenzo[h]isoquinolin-7-yl]imidazole-4-carboxylate.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

The following examples illustrate how the compounds covered by formula I may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Abbreviations

DCM Dichloromethane
THF Tetrahydrofuran
EtOAc Ethyl acetate
MeCN Acetonitrile
MeOH Methanol
M Mass or Molar
Brine Saturated sodium chloride solution
HPLC High performance liquid chromatography
LCMS Liquid Chromatography Mass Spectrometry
DIPEA N,N-di-iso-propylethylamine
RT Retention time
DMF N, N'-dimethylformamide
sat. saturated
aq. aqueous
tBuXPhos Pd G3 [(2-Di-tert-butylphosphino-2',4',6'-triisopropyl-1,1'-biphenyl)-2-(2'-amino-1,1' biphenyl)] palladium(II)methanesulfonate
IPA Isopropyl alcohol
conc. concentrated
SCX Biotage® SOLUTE® SCX-2 Propylsulfonic acid functionalized silica
TEA Triethylamine
AcOH Acetic acid
AIBN 2,2'-Azobis(2-methylpropionitrile)
Bedford Catalyst Chloro($\eta^2$-P,C-tris(2,4-di-tert butylphenyl)phosphite)(tricyclohexylphosphine)palladium(II)
NBS N-Bromosuccinimide
min minutes LCMS Methods Method 1:

X-Bridge C18 Waters 2.1×20 mm, 2.5 μm column

Column Temperature 40° C.

Mobile Phase A: 10 mM Ammonium formate in water+0.1% formic acid

Mobile Phase B: Acetonitrile+5% water+0.1% formic acid

Gradient program: Flow rate 1 mL/minute

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 2:

Mobile Phase A: 0.1% Formic Acid in water

Mobile Phase B: 0.1% Formic Acid in Acetonitrile

Phenomenex, Kinetex-XB C18, 2.1 mm×100 mm, 1.7 μm column

Flow rate: 0.6 mL/min

Column temperature: 40° C.

Injection volume: 1 μL

Gradient:

| Time (minutes): | % A | % B |
|---|---|---|
| 0.00 | 95 | 5 |
| 5.30 | 0 | 100 |
| 5.80 | 0 | 100 |
| 5.82 | 95 | 5 |
| 7.00 | 95 | 5 |

UV 215 nM, PDA spectrum 200-400 nm, step: 1 nm

MSD Scan Positive 150-850

Method 3:

X-Bridge C18 Waters 2.1×20 mm, 2.5 μM column

Column Temperature 40° C.

Mobile Phase A: 10 mM Ammonium formate in water+0.1% formic acid

Mobile Phase B: Acetonitrile+5% water+0.1% Formic acid

Gradient program: Flow rate 1 mL/min

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 4:

Stationary phase: X-Bridge C18 Waters 2.1×20 mm, 2.5 μM column

Mobile Phase A: 10 mM Ammonium formate in water+0.1% Ammonia solution

Mobile Phase B: Acetonitrile+5% water+0.1% Ammonia Solution

Flow rate: 1 mL/min

Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 5:

System: Waters Classic Acquity-QDa, Acquity PDA

Stationary phase: Waters Acquity UPLC BEH, C18, 2.1×50 mm, 1.7 μm

Mobile Phase A: 10 mM Ammonium Formate in water+0.1% Ammonia Solution

Mobile Phase B: Acetonitrile+5% water+0.1% Ammonia Solution

Flow rate: 0.7 mL/min

Temp: 40° C.

Gradient program:

| Time | A % | B % |
|---|---|---|
| 0.00 | 98.00 | 2.00 |
| 4.00 | 5.00 | 95.00 |
| 5.00 | 5.00 | 95.00 |
| 5.10 | 98.00 | 2.00 |

Method 6:

Stationary phase: X-Bridge C18 Waters 2.1×20 mm, 2.5 μM column

Mobile Phase A: 10 mM Ammonium formate in water+0.1% Formic acid

Mobile Phase B: Acetonitrile+5% water+0.1% Formic acid

Flow rate: Pump 1:1 mL/min, Pump 2:0.5 mL/min

Gradient program:

| Pump 1: | | | Pump 2: | | |
|---|---|---|---|---|---|
| Time | A % | B % | Time | A % | B % |
| 0.00 | 95.10 | 4.90 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.10 | 4.90 | | | |

Method 7:

Stationary phase: X-Bridge C18 Waters 2.1×20 mm, 2.5 μM column

Mobile Phase A: 10 mM Ammonium formate in water+0.1% ammonia solution

Mobile Phase B: Acetonitrile+5% water+0.1% Ammonia Solution

Flow rate: 1 mL/min

Gradient program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 8:

Stationary phase: X-Bridge C18 Waters 2.1×20 mm, 2.5 μM column

Mobile Phase A: 10 mM Ammonium formate in water+0.1% Ammonia solution

Mobile Phase B: Acetonitrile+5% water+0.1% Ammonia solution

Flow rate: Pump 1:1 mL/min, Pump 2:0.5 mL/min

Gradient program:

| Pump 1: | | | Pump 2: | | |
|---|---|---|---|---|---|
| Time | A % | B % | Time | A % | B % |
| 0.00 | 95.10 | 4.90 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.10 | 4.90 | | | |

Method 9:

Stationary phase: X-Bridge C18 Waters 2.1×20 mm, 2.5 μM column

Mobile Phase A: 10 mM Ammonium formate in water+0.1% Ammonia solution

Mobile Phase B: Acetonitrile+5% water+0.1% Ammonia Solution

Flow rate: 1 mL/min

Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Intermediates

Intermediate 1

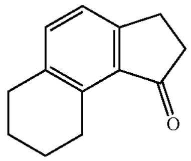 [SMILES: O=C1CCc2ccc3c(c21)CCCC3]

2,3,6,7,8,9-hexahydrocyclopenta[a]naphthalen-1-one 1,2,3,4-tetrahydronaphthalene (5.17 mL, 37.8 mmol) was added slowly to a suspension of $AlCl_3$ (10.6 g, 79.4 mmol) and prop-2-enoyl chloride (3.4 mL, 41.6 mmol) in DCM (300 mL) at −78° C. The mixture was subsequently allowed to warm to room temperature overnight. The solution was carefully hydrolysed on ice and organic phase separated. The aq. phase was extracted twice with DCM and the combined organic fractions were washed with an aqueous solution of potassium carbonate and dried over sodium sulfate. The solvent was removed under vacuum and the crude reside purified by column chromatography, eluting with a gradient of 0% to 20% EtOAc in heptane to afford the title compound (1.01 g, 12% Yield). LCMS $[M+H]^+$ 187, RT 1.89 min (Method 1).

Intermediate 2

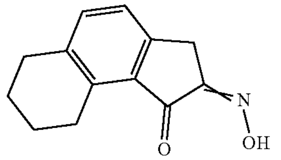 [SMILES: O=C1C(=NO)Cc2ccc3c(c21)CCCC3]

2-hydroxyimino-6,7,8,9-tetrahydro-3H-cyclopenta[a]naphthalen-1-one

To a solution of Intermediate 1 (1.0 g, 5.36 mmol) in ether (13 mL), first saturated ethanolic HCl (0.22 mL) and then 15% ethanolic soliton of ethyl nitrite (4.81 mL, 7.62 mmol) were added dropwise at 0° C. After 30 minutes at 0° C., the precipitated product was collected by filtration, washed with ether and dried to give the crude title compound (1.15 g, 74% yield), which was used in the next stage without further purification. LCMS $[M+H]^+$ 216, RT 1.77 min (Method 1).

Intermediate 3

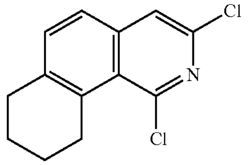 [SMILES: Clc1cc2ccc3c(c2c(Cl)n1)CCCC3]

1,3-dichloro-7,8,9,10-tetrahydrobenzo[h]isoquinoline

To a suspension of Intermediate 2 (0.86 g, 3.99 mmol) in $POCl_3$ (24 mL), $PCl_5$ (940 mg, 4.51 mmol) was added at 0° C. Then gaseous HCl was introduced until the solution was saturated and the reaction stirred at 60° C. for 4 hours. Then again $PCl_5$ (316 mg) was added and stirring was continued for 2 hours at 80° C. The solvent was removed under vacuum and the residue slowly hydrolysed by addition of water to give a precipitate which was collected by filtration. The collected solid was washed with water and dried to give the crude title compound (1 g, 84% yield), which was used in the next stage without further purification. LCMS $[M+H]^+$ 252, RT 2.50 min (Method 1).

Intermediate 4

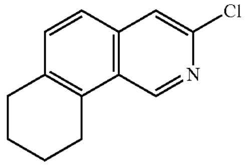 [SMILES: Clc1cc2ccc3c(c2cn1)CCCC3]

3-chloro-7,8,9,10-tetrahydrobenzo[h]isoquinoline

A mixture of Intermediate 3 (0.88 g, 3.52 mmol), a solution of red phosphorus (261 mg, 8.45 mmol) in AcOH (4 mL) and HI (57%) (1.59 mL, 12.1 mmol) was refluxed for 8 hours. The hot reaction mixture was filtered, evaporated, the residue was dissolved in water and basified by addition of conc. aq. $NH_4OH$. The precipitate was collected by filtration, dissolved in DCM, washed with brine, dried over $MgSO_4$ and evaporated. The resulting crude residue was purified by column chromatography eluting with a gradient of 8% to 40% EtOAc in heptane to afford the title compound (600 mg, 74% yield). LCMS $[M+H]^+$ 218, RT 2.03 min (Method 1).

Intermediate 5

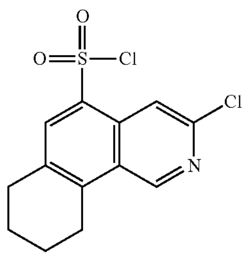 [SMILES: O=S(=O)(Cl)c1cc2c(c3cnc(Cl)cc13)CCCC2]

3-chloro-7,8,9,10-tetrahydrobenzo[h]isoquinoline-5-sulfonyl chloride

A mixture of intermediate 4 (15.0 g, 68.9 mmol) and chlorosulfonic acid (55 mL, 819 mmol) was heated at 80° C. in a sealed tube for 3 hours 15 min. The reaction mixture was then diluted with DCM (400 mL) and poured into $H_2O$ (400 mL) at 0° C. The phases were separated and the aqueous was extracted with DCM (4×100 mL), the organics combined, dried ($Na_2SO_4$), filtered and conc. in vacuo to give crude the title compound (21.8 g, assumed quantitative) which was taken onto the next step without further purification. LCMS $[M+H]^+$ 353 (quenched with $^t$BuN $H_2$), RT 1.33 min (Method 4).

Intermediate 6

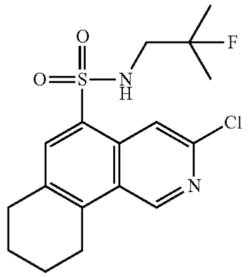 [SMILES: CC(C)(F)CNS(=O)(=O)c1cc2c(c3cnc(Cl)cc13)CCCC2]

3-chloro-N-(2-fluoro-2-methyl-propyl)-7,8,9,10-tetrahydrobenzo[h]isoquinoline-5-sulfonamide To a stirred solution of intermediate 5 (21.8 g, 68.9 mmol) in DCM (250 mL) at 0° C. were added 2-fluoro-2-methyl-propan-1-amine HCl (9.85 g, 77.2 mmol) followed by DIPEA (30 mL, 172 mmol). The reaction was then stirred at room temperature for 15 hours. The mixture was diluted with $H_2O$ (200 mL), brine (200 mL) and the phases separated. The aqueous phase was extracted with DCM (2×50 mL), and the combined organics extracted with $H_2O$ (150 mL) then brine (150 mL), dried and concentrated in vacuo. The resultant solid was triturated with an 8:2 mixture of EtOAc:iso-hexane (100 mL) to give the title compound (19.7 g, 73% Yield). The filtrate was conc in vacuo and purified by column chromatography eluting with 0-50% EtOAc in iso-hexane to give a second crop of the title compound (3.7 g, 12% Yield). LCMS $[M+H]^+$ 371, RT 1.23 min (Method 4).

Intermediates 7 & 8

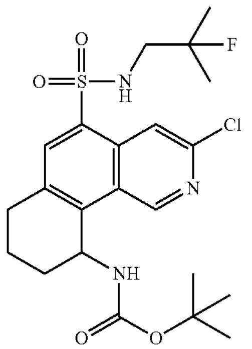

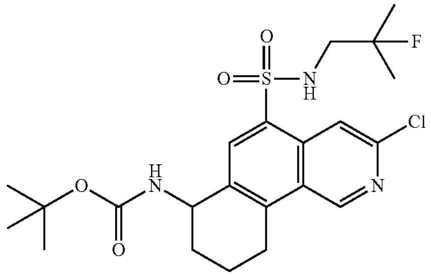

tert-butyl N-[3-chloro-5-[(2-fluoro-2-methyl-propyl) sulfamoyl]-7,8,9,10-tetrahydrobenzol[h]ilisoquinolin-10-yl]carbamate (7)

tert-butyl N-[3-chloro-5-[(2-fluoro-2-methyl-propyl) sulfamoyl]-7,8,9,10-tetrahydrobenzo[h]isoquinolin-7-yl]carbamate (8)

To a solution of intermediate 6 (9.10 g, 24.5 mmol) in EtOAc (235 mL) at 50° C. were added NBS (4.85 g, 27.2 mmol) and 2,2'-azobis(2-methylpropionitrile) (400 mg, 2.44 mmol). The reaction mixture was heated to 90° C. under $N_2$ for 2.5 hours. The mixture was conc. in vacuo the reside dissolved in THF (200 mL), purged with $NH_3$ gas for 10 min then heated at 70° C. in a sealed vessel for 11 hours. The mixture was then conc. in vacuo, suspended in DCM (200 mL) in an ice-bath, to which was then added a solution of di-tert-butyl dicarbonate (7.9 g, 35 mmol) in DCM (30 mL) followed by TEA (9 mL, 64.6 mmol). After 4 h, further di-tert-butyl dicarbonate (1.0 g, 4.4 mmol) was added and the reaction stirred for 3 days. The reaction mixture was then diluted with brine (200 mL), sat. $NaHCO_3$ (200 mL) and the phases separated. The aqueous was extracted with DCM (3×50 mL), and the combined organics dried and conc. in vacuo. Purification by column chromatography eluting with 0-20% EtOAc in iso-hexane gave the title compounds:

Intermediate 7 (2.35 g, 19% Yield); LCMS $[M+H]^+$ 486, RT 1.28 (Method 4).

Intermediate 8 (3.53 g, 27% Yield); LCMS $[M+H]^+$ 486, RT 1.23 (Method 4).

Intermediate 9

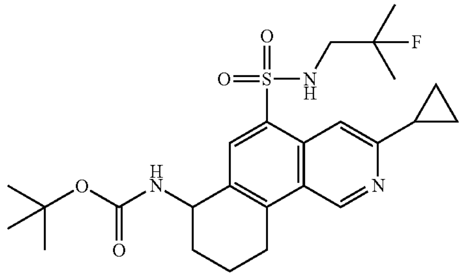 [SMILES: CC(C)(F)CNS(=O)(=O)c1cc2c(c3cnc(C4CC4)cc13)CCCC2NC(=O)OC(C)(C)C]

tert-butyl N-[3-cyclopropyl-5-[(2-fluoro-2-methyl-propyl)sulfamoyl]-7,8,9,10-tetrahydrobenzo[h]isoquinolin-7-yl]carbamate To a suspension of intermediate 8 (3.52 g, 6.52 mmol) in a mixture of toluene (70 mL), 1,4-dioxane (40 mL) and $H_2O$ (3.5 mL) were added cyclopropylboronic acid (1.87 g, 21.8 mmol) and potassium phosphate tribasic (3.95 g, 18.2 mmol). The mixture was purged with $N_2$ for 5 min followed by the addition of palladium(II) acetate (90 mg, 0.40 mmol) and tricyclohexylphosphonium tetrafluoroborate (400 mg, 1.05 mmol). The resultant orange mixture was purged with $N_2$ for 5 min then heated at 120° C. for 11 hours after which further palladium (II) acetate (90 mg, 0.40 mmol) and tricyclohexylphosphonium tetrafluoroborate (400 mg, 1.05 mmol) were added and the mixture purged with $N_2$ for a further 5 min then heated at 120° C. for 3 days. The reaction mixture was conc. in vacuo and the residue taken up in EtOAc (400 mL containing a few millilitres of IPA). Water (150 mL) and brine (200 mL) were added and the phases separated. The aqueous phase was extracted with EtOAc (100 mL) and the combined organics dried, conc. in vacuo and triturated with $Et_2O$ (150 mL) to give the title compound (2.20 g, 69% Yield). LCMS $[M+H]^+$ 492, RT 1.25 min (Method 4).

Intermediate 10

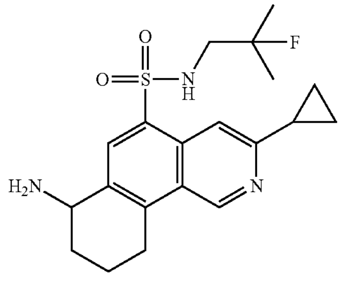 [SMILES: CC(C)(F)CNS(=O)(=O)c1cc2c(c3cnc(C4CC4)cc13)CCCC2N]

7-amino-3-cyclopropyl-N-(2-fluoro-2-methyl-propyl)-7,8,9,10-tetrahydrobenzo[h]isoquinoline-5-sulfonamide Hydrochloric acid (4 N in dioxane, 6 mL) was added to intermediate 9 (500 mg, 0.98 mmol) followed by MeOH (2 mL) and the resultant solution stirred at room temperature for 1.5 hours. The reaction mixture was conc. in vacuo and passed through a 10 g SCX cartridge eluting with 7 N $NH_3$ in MeOH then triturated with $Et_2O$ (20 mL) to give the title compound (356 mg, 93% Yield). LCMS $[M+H]^+$ 392, RT 1.32 min (Method 9).

Intermediate 11

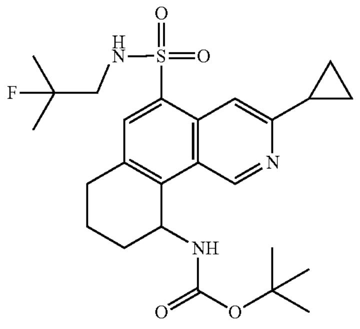 [SMILES: CC(C)(F)CNS(=O)(=O)c1cc2c(c3cnc(C4CC4)cc13)C(NC(=O)OC(C)(C)C)CCC2]

tert-butyl N-[3-cyclopropyl-5-[(2-fluoro-2-methyl-propbyl)sulfamoyl]-7,8,9,10-tetrahydrobenzo[h]isoquinolin-10-yl]carbamate To a suspension of intermediate 7 (2.35 g, 4.84 mmol) in a mixture of toluene (50 mL), 1,4-dioxane (20 mL) and $H_2O$ (3 mL) were added cyclopropylboronic acid (1.2 g, 14 mmol) and potassium phosphate tribasic (2.6 g, 12 mmol). The mixture was purged with $N_2$ for 5 min followed by the addition of palladium (II) acetate (55 mg, 0.24 mmol) and tricyclohexylphosphonium tetrafluoroborate (270 mg, 0.71 mmol). The resultant orange mixture was purged with $N_2$ for 5 min then heated at 120° C. for 9 hours after which further palladium (II) acetate (55 mg, 0.24 mmol) and tricyclohexylphosphonium tetrafluoroborate (270 mg, 0.71 mmol) were added and the mixture purged with $N_2$ for a further 5 min then heated at 120° C. for 8 hours. The reaction mixture was conc. in vacuo, taken up in EtOAc (400 mL) and washed with brine (150 mL). The phases were separated and the aqueous was extracted with EtOAc (2×100 mL). The combined organics were dried, conc. in vacuo and triturated with $Et_2O$ (100 mL) to give the title compound (1.96 g, 82% Yield). LCMS $[M+H]^+$492, RT 1.29 min (Method 4).

Intermediate 12

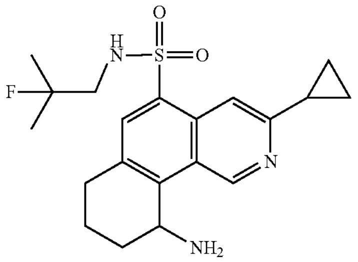 [SMILES: CC(C)(F)CNS(=O)(=O)c1cc2c(c3cnc(C4CC4)cc13)C(N)CCC2]

10-amino-3-cyclopropyl-N-(2-fluoro-2-methyl-propyl)-7,8,9,10-tetrahydrobenzo[h]isoquinoline-5-sulfonamide Hydrochloric acid (4 N in dioxane, 6 mL) was added to intermediate 11 (500 mg, 1.00 mmol) followed by MeOH (2 mL) and the solution stirred at room temperature for 1 hour. The reaction mixture was conc. in vacuo and passed through an SCX cartridge eluting with 7 N $NH_3$ in MeOH then triturated with $Et_2O$ (10 mL) to give the title compound (307 mg, 75% Yield). LCMS $[M+H]^+$ 392, RT 0.97 min (Method 4).

Intermediate 13

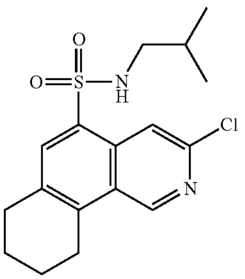 [SMILES: CC(C)CNS(=O)(=O)c1cc2c(c3cnc(Cl)cc13)CCCC2]

3-chloro-N-isobutyl-7,8,9,10-tetrahydrobenzo[h]isoquinoline-5-sulfonamide

To a solution of Intermediate 5 (475 mg, 1.50 mmol) in DCM (20 mL), 2-methylpropan-1-amine (0.74 mL, 7.51 mmol) was added dropwise and reaction mixture was stirred at room temperature for 2 hours. The reaction mixture was diluted with DCM (50 mL) and washed with water. The organic layer was dried over $MgSO_4$ and concentrated under reduced pressure. The residue was then purified by column chromatography eluting with a gradient of 12% to 60% EtOAc in heptane to afford the title compound (497 mg, 92% yield). LCMS $[M+H]^+$ 353, RT 3.97 min (Method 2).

Intermediates 14 & 15

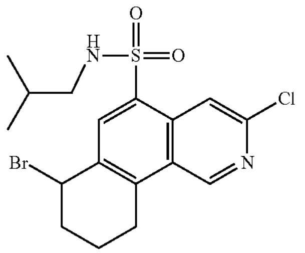

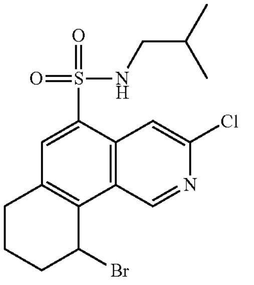

7-bromo-3-chloro-N-isobutyl-7,8,9,10-tetrahydrobenzo[h]isoquinoline-5-sulfonamide (14)

10-bromo-3-chloro-N-isobutyl-7,8,9,10-tetrahydrobenzo[h]isoquinoline-5-sulfonamide (15)

Intermediate 13 (150 mg, 0.42 mmol) was dissolved in EtOAc (15 mL) and NBS (75.6 mg, 0.42 mmol) followed by AIBN (6.98 mg, 0.043 mmol) were added. The heterogeneous mixture was heated to 90° C. for 3 hours. Reaction mixture was diluted with EtOAc and washed with aq. $Na_2S_2O_3$, water and brine. The organic layer was dried over $MgSO_4$ and concentrated under reduced pressure. The crude reside was purified by column chromatography eluting with a gradient of 0% to 50% EtOAc in heptane to afford the title compounds (145 mg, 56% yield) as a mixture of regio-isomers in 71% purity. LCMS $[M+H]^+$ 431/433, RT 3.33 min (Method 3) [Note: both regio-isomers co-eluted same RT].

Intermediates 16 & 17

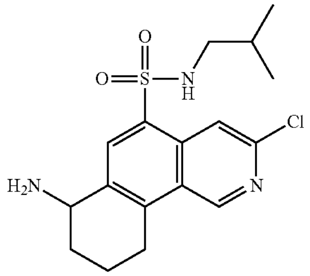

-continued

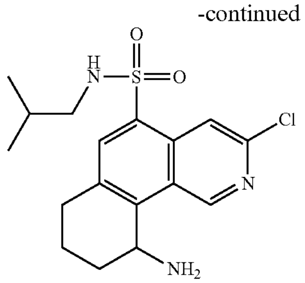

7-amino-3-chloro-N-isobutyl-7,8,9,10-tetrahydrobenzo[h]isoquinoline-5-sulfonamide (16)

10-amino-3-chloro-N-isobutyl-7,8,9,10-tetrahydrobenzol[h]isoquinoline-5-sulfonamide (17)

A mixture of intermediates 14 & 15 (71%, 145 mg, 0.24 mmol) was dissolved in ammonia 7 N in MeOH (2 mL) and stirred at room temperature for 16 hours. The solvent was removed under vacuum and DCM followed by water were added. The organic layer was separated, dried over $Na_2SO_4$ and concentrated under reduced pressure. The crude residue was purified by column chromatography eluting first with a gradient of 5% to 100% EtOAc in heptane to remove the non-brominated starting material, then eluting with a gradient of 0% to 10% MeOH in DCM to afford the title compounds (84 mg, 94% yield) as mixture of regio-isomers. LCMS $[M+H]^+$ 368, RT 2.09 and 2.14 min (Method 3).

Intermediates 18 & 19

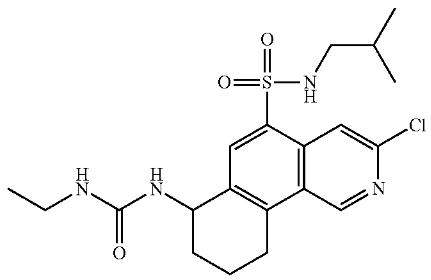

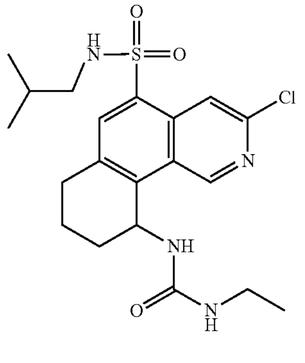

1-[3-chloro-5-(isobutylsulfamoyl)-7,8,9,10-tetrahydrobenzo[h]isoquinolin-7-yl]-3-ethyl-urea (18)

1-[3-chloro-5-(isobutylsulfamoyl)-7,8,9,10-tetrahydrobenzo[h]isoquinolin-10-yl]-3-ethyl-urea (19)

Isocyanatoethane (19.8 μL, 0.25 mmol) was added to a mixture of intermediates 16 & 17 (84 mg, 0.22 mmol) in DCM (4 mL). The solution was stirred at room temperature for 5 hours after which time a precipitate had appeared. MeOH (5 mL) was added. Then solvents were removed, and the crude was purified by acidic reverse phase HPLC to afford the title compounds:

Intermediate 18 (37 mg, 70% yield). LCMS $[M+H]^+$ 439, RT 2.63 min (Method 3).

Intermediate 19 (24 mg, 44% yield). LCMS $[M+H]^+$ 439, RT 2.70 min (Method 3).

Intermediates 20 & 21

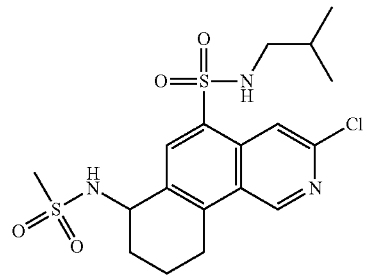

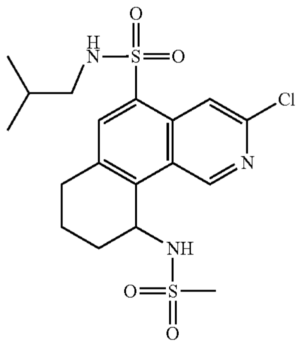

3-chloro-N-isobutyl-7-(methanesulfonamido)-7,8,9,10-tetrahydrobenzo[h]isoquinoline-5-sulfonamide (20)

3-chloro-N-isobutyl-10-(methanesulfonamido)-7,8,9,10-tetrahydrobenzo[h]isoquinoline-5-sulfonamide (21)

DIPEA (103.4 μL, 0.58 mmol) followed by methanesulphonyl chloride (23 μL, 0.29 mmol) were added to a mixture of intermediates 16 & 17 (120 mg, 0.29 mmol) in DCM (4 mL). The reaction mixture was stirred at room temperature for 4 hours. The reaction mixture was then diluted with DCM and water. The organic layer was separated, dried over $Na_2SO_4$, and concentrated under reduced pressure. Purification by reverse phase HPLC (acidic conditions) afforded the title compounds:

Intermediate 20 (65 mg, 98% yield). LCMS $[M+H]^+$ 446, RT 2.68 min (Method 3).

Intermediate 21 (31 mg, 43% yield). LCMS $[M+H]^+$ 446, RT 2.74 min (Method 3).

Intermediate 22

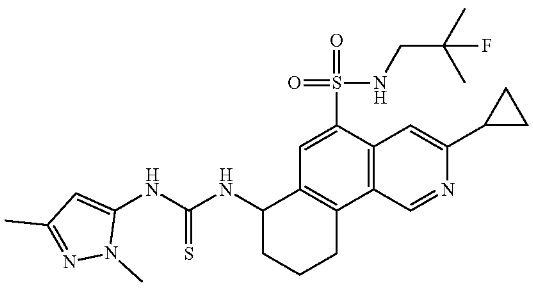

1-[3-cyclopropyl-5-[(2-fluoro-2-methyl-propyl)sulfamoyl]-7,8,9,10-tetrahydrobenzo[h]isoquinolin-7-yl]-3-(2,5-dimethylpyrazol-3-yl) thiourea To a vessel charged with 5-isothiocyanato-1,3-dimethyl-pyrazole (25 mg, 0.16 mmol) was added a suspension of intermediate 10 (50 mg, 0.13 mmol) in DCM (1 mL) and THF (2 mL). The resultant reaction mixture was stirred at room temperature for 3 days then filtered to obtain the title compound (56 mg, 76% Yield). LCMS $[M+H]^+$ 545, RT 1.11 min (Method 4).

EXAMPLES

Example 1

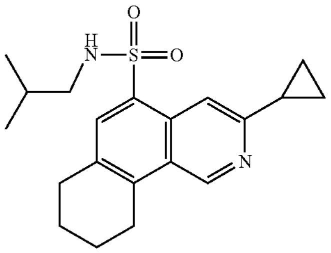 [SMILES: CC(C)CNS(=O)(=O)c1cc2c(c3cnc(C4CC4)cc13)CCCC2]

3-cyclopropyl-N-(2-methylpropyl)-7,8,9,10-tetrahydrobenzo[h]isoquinoline-5-sulfonamide A mixture of Intermediate 13 (100 mg, 0.28 mmol) and cyclopropyl boronic acid (48.6 mg, 0.56 mmol) was dissolved in nitrogen sparged dioxane (5 mL). A 2 M aq. solution of $K_2CO_3$ (0.42 mL, 0.85 mmol) was then added followed by Bedford catalyst (30.2 mg, 0.028 mmol). The reaction mixture was stirred at 100° C. for 16 hours under an atmosphere of $N_2$, then concentrated under reduced pressure to remove the dioxane. The residual solution was diluted with DCM (20 mL) and the organic layer washed with water, dried over $MgSO_4$ and concentrated under reduced pressure. Purification by reverse phase HPLC (basic conditions) afforded the title compound (41 mg, 40% yield). $\delta_H$ (500 MHz, Chloroform-d) 9.39 (s, 1H), 8.18 (s, 1H), 8.09 (s, 1H), 4.61 (t, J=6.5 Hz 1H), 3.24 (t, J=6.3 Hz, 2H), 2.93 (t, J=6.1 Hz, 2H), 2.70 (t, J=6.6 Hz, 2H), 2.28-2.18 (m, 1H), 2.02-1.95 (m, 2H), 1.94-1.86 (m, 2H), 1.73-1.64 (m, 1H), 1.17-1.10 (m, 2H), 1.10-1.03 (m, 2H), 0.83 (d, J=6.7 Hz, 6H). LCMS $[M+H]^{30}$ 359, RT 3.67 min (Method 2).

Example 2

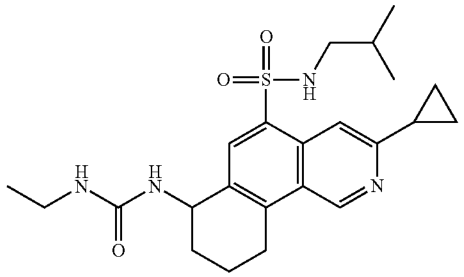 [SMILES: CCNC(=O)NC1CCCc2c1cc(S(=O)(=O)NCC(C)C)c1cc(C3CC3)ncc21]

1-[3-cyclopropyl-5-(2-methylpropylsulfamoyl)-7,8,9,10-tetrahydrobenzo[h]isoquinolin-7-yl]-3-ethyl-urea A mixture of Intermediate 16 (35 mg, 0.08 mmol) and cyclopropyl boronic acid (13.7 mg, 0.15 mmol) was dissolved in nitrogen sparged dioxane (2 mL). An aq. 2 M solution of $K_2CO_3$ (119.6 μL, 0.23 mmol) was then added followed by Bedford catalyst (8.5 mg, 0.008 mmol). The mixture was stirred at 120° C. in the microwave for 2 hours under an atmosphere of $N_2$. The reaction mixture was concentrated under reduced pressure to remove the dioxane. The residual solution was diluted with DCM (15 mL) and the organic layer washed with water, dried over $MgSO_4$ and concentrated under reduced pressure. Purification by reverse phase HPLC (acidic conditions) afforded the title compound (4 mg, 11% yield). $\delta_H$ (500 MHz, Chloroform-d) 9.30 (s, 1H), 8.30 (s, 1H), 8.20 (s, 1H), 5.15-5.07 (m, 1H), 5.05-4.96 (m, 1H), 4.92-4.82 (m, 1H), 4.67-4.57 (m, 1H), 3.32-3.06 (m, 4H), 2.86-2.76 (m, 1H), 2.73-2.64 (m, 1H), 2.27-2.19 (m, 1H), 2.16-2.07 (m, 1H), 2.06-1.91 (m, 2H), 1.88-1.79 (m, 1H), 1.75-1.66 (m, 1H), 1.19-1.00 (m, 7H), 0.91-0.80 (m, 6H). LCMS $[M+H]^+$ 445, RT 2.70 min (Method 2).

Example 3

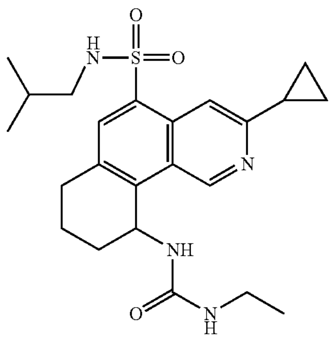 [SMILES: CCNC(=O)NC1CCCc2cc(S(=O)(=O)NCC(C)C)c3cc(C4CC4)ncc3c21]

1-[3-cyclopropyl-5-(2-methylpropylsulfamoyl)-7,8,9,10-tetrahydrobenzo[h]isoquinolin-10-yl]-3-ethyl-urea A mixture of intermediate 17 (20 mg, 0.046 mmol) and cyclopropyl boronic acid (7.8 mg, 0.091 mmol) was dissolved in nitrogen sparged dioxane (2 mL). An aq. 2 M solution of $K_2CO_3$ (68.3 μL, 0.23 mmol) was added followed by Bedford catalyst (4.8 mg, 0.005 mmol). The mixture was stirred at 120° C. in a microwave for 2 hours under an atmosphere of nitrogen. The reaction mixture was concentrated under reduced pressure to remove the dioxane. The residual solution was diluted with DCM (15 mL) and the organic layer washed with water, dried over $MgSO_4$ and concentrated under reduced pressure. Purification by reverse phase HPLC (acidic conditions) afforded the title compound (6 mg, 30% yield). $\delta_H$ (500 MHz, Methanol-d4) 9.35 (s, 1H), 8.31 (s, 1H), 8.08 (s, 1H), 5.82-5.49 (m, 1H), 3.24-3.12 (m, 2H), 3.06-2.98 (m, 1H), 2.98-2.88 (m, 1H), 2.63 (d, J=6.9 Hz, 2H), 2.32-2.22 (m, 1H), 2.21-2.10 (m, 1H), 2.07-1.80 (m, 3H), 1.71-1.55 (m, 1H), 1.22-0.99 (m, 7H), 0.82-0.76 (m, 6H). LCMS $[M+H]^+$ 445, RT 2.78 min (Method 2).

Example 4

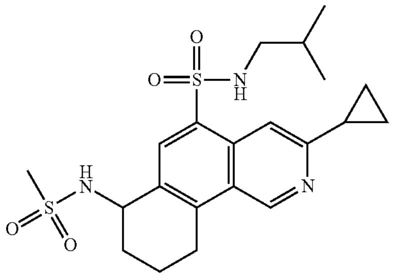 [SMILES: CC(C)CNS(=O)(=O)c1cc2c(c3cnc(C4CC4)cc13)CCCC2NS(C)(=O)=O]

3-cyclopropyl-7-(methanesulfonamido)-N-(2-methylpropyl)-7,8,9,10-tetrahydrobenzo[h]isoquinoline-5-sulfonamide A mixture of intermediate 16 (63 mg, 0.14 mmol) and cyclopropyl boronic acid (24.2 mg, 0.28 mmol) was dissolved in nitrogen sparged dioxane (3 mL). An aq. 2 M solution of $K_2CO_3$ (0.21 mL, 0.42 mmol) was added followed by Bedford catalyst (15.1 mg, 0.014 mmol). The reaction mixture was concentrated under reduced pressure to remove the dioxane. The residual solution was diluted with DCM (20 mL) and the organic layer washed with water, dried over $MgSO_4$ and concentrated under reduced pressure. Purification by reverse phase HPLC (acidic conditions) afforded the title compound (27 mg, 41% yield). $\delta_H$ (500 MHz, Chloroform-d) 9.35 (s, 1H), 8.34 (s, 1H), 8.22 (s, 1H), 4.91-4.72 (m, 3H), 3.32-3.22 (m, 1H), 3.21-3.08 (m, 4H), 2.94-2.70 (m, 2H), 2.33-2.15 (m, 2H), 2.11-1.95 (m, 3H), 1.83-1.69 (m, 1H), 1.19-1.13 (m, 2H), 1.12-1.06 (m, 2H), 0.91-0.84 (m, 6H). LCMS $[M+H]^+$ 452, RT 2.89 min (Method 2).

Example 5

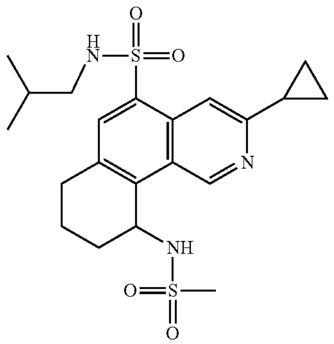 [SMILES: CC(C)CNS(=O)(=O)c1cc2c(c3cnc(C4CC4)cc13)C(NS(C)(=O)=O)CCC2]

3-cyclopropyl-10-(methanesulfonamido)-N-(2-methylpropyl)-7,8,9,10-tetrahydrobenzol[h]isoquinoline-5-sulfonamide A mixture of intermediate 17 (30 mg, 0.067 mmol) and cyclopropyl boronic acid (11.56 mg, 0.13 mmol) was dissolved in nitrogen sparged dioxane (2 mL). An aq. 2 M solution of $K_2CO_3$ (0.10 mL, 0.20 mmol) was added followed by Bedford catalyst (7.1 mg, 0.007 mmol). The mixture was stirred at 120° C. in microwave for 2 hours under an atmosphere of nitrogen. The reaction mixture was concentrated under reduced pressure to remove the dioxane. The residual solution was diluted with DCM (15 mL) and the organic layer washed with water, dried over $MgSO_4$ and concentrated under reduced pressure. Purification by reverse phase HPLC (acidic conditions) afforded the title compound (10 mg, 33% yield). $\delta_H$ (500 MHz, Chloroform-d) 9.60 (s, 1H), 8.18 (s, 1H), 8.08 (s, 1H), 5.59-5.53 (m, 1H), 4.66 (t, J=6.2 Hz, 1H), 4.54 (d, J=7.3 Hz, 1H), 3.13 (s, 3H), 3.07-3.00 (m, 1H), 2.99-2.89 (m, 1H), 2.71 (t, J=6.6 Hz, 2H), 2.50-2.44 (m, 1H), 2.24-2.18 (m, 1H), 2.09-2.00 (m, 2H), 1.98-1.89 (m, 1H), 1.76-1.67 (m, 1H), 1.20-1.13 (m, 2H), 1.11-1.04 (m, 2H), 0.85 (d, J=6.7 Hz, 6H). LCMS $[M+H]^+$ 452, RT 2.94 min (Method 2).

Example 6

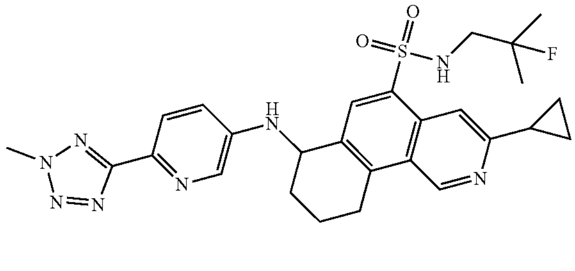 [SMILES: Cn1nnc(-c2ccc(NC3CCCc4c3cc(S(=O)(=O)NCC(C)(C)F)c3cc(C5CC5)ncc43)cn2)n1]

3-cyclopropyl-N-(2-fluoro-2-methylpropyl)-7-[[6-(2-methyltetrazol-5-yl)pyridin-3-yl)]amino]-7,8,9,10-tetrahydrobenzo[h]isoquinoline-5-sulfonamide To a stirred suspension of intermediate 10 (30 mg, 0.08 mmol) in anhydrous 1,4-dioxane (2.5 mL) at room temperature were added 5-bromo-2-(2-methyltetrazol-5-yl)pyridine (37 mg, 0.15 mmol), sodium tert-butoxide (22 mg, 0.23 mmol) and tBuXPhos Pd G3 (9 mg, 0.01 mmol). The resultant mixture was purged with $N_2$ for 10 min. After a further 15 min, the reaction mixture was filtered through celite and conc. in vacuo. Purification by column chromatography eluting with 0-20% MeOH in EtOAc followed by basic reverse phase column chromatography gave the title compound (20 mg, 44% Yield). $\delta_H$ (300 MHz, d6-DMSO) 9.48 (s, 1H), 8.36 (s, 2H), 8.22 (d, J=2.7 Hz, 1H), 8.15 (s, 1H), 7.88 (d, J=8.6 Hz, 1H), 7.24 (dd, J=8.8, 2.8 Hz, 1H), 6.93 (d, J=8.7 Hz, 1H), 4.95 (d, J=8.6 Hz, 1H), 4.39 (s, 3H), 3.39 (s, 1H), 3.20 (d, J=18.0 Hz, 1H), 2.96-2.79 (m, 2H), 2.34-2.25 (m, 1H), 1.97 (s, 4H), 1.19 (dd, J=21.4, 3.2 Hz, 6H), 1.06 (d, J=6.3 Hz, 4H). LCMS $[M-H]^-$ 549, RT 2.16 min (Method 8).

Example 7

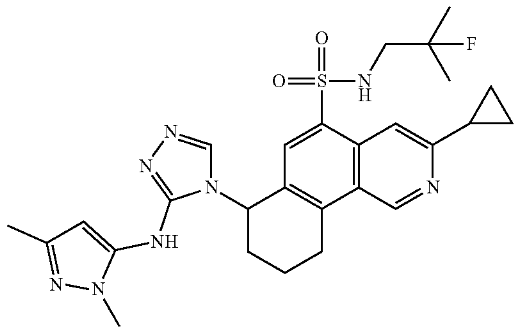 [SMILES: Cc1cc(Nc2nncn2C2CCCc3c2cc(S(=O)(=O)NCC(C)(C)F)c2cc(C4CC4)ncc32)n(C)n1]

3-cyclopropyl-7-[3-[(2,5-dimethylpyrazol-3-yl)amino]-1,2,4-triazol-4-yl]-N-(2-fluoro-2-methylpropyl)-7,8,9,10-tetrahydrobenzo[h]isoquinoline-5-sulfonamide To a solution of intermediate 22 (55 mg, 0.10 mmol) in DMF (1 mL) were added formic acid hydrazide (18 mg, 0.30 mmol) and mercuric chloride (52 mg, 0.19 mmol). TEA (40 µL, 0.29 mmol) was then added and the reaction mixture was heated at 80° C. for 4 hours. The reaction mixture was then filtered through celite (20 mL MeCN washings) and conc. in vacuo. Purification by column chromatography gave the title compound (10 mg, 19% Yield). $\delta_H$ (300 MHz, d6-DMSO) 9.51 (s, 1H), 8.54 (s, 1H), 8.35 (s, 1H), 7.89 (s, 1H), 7.75 (s, 1H), 5.85 (s, 1H), 5.67 (s, 1H), 3.38 (s, 5H), 2.78 (d, J=20.0 Hz, 2H), 2.29 (q, J=6.1 Hz, 1H), 2.20 (s, 2H), 2.07 (s, 3H), 1.98 (s, 2H), 1.13 (dd, J=21.4, 4.9 Hz, 6H), 1.07 (d, J=6.6 Hz, 4H). [one H not visible]. LCMS $[M+H]^+$ 553, RT 2.14 min (Method 5).

Example 8

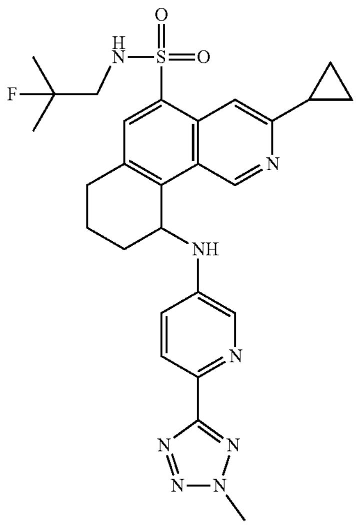 [SMILES: Cn1nnc(-c2ccc(NC3CCCc4cc(S(=O)(=O)NCC(C)(C)F)c5cc(C6CC6)ncc5c43)cn2)n1]

3-cyclopropyl-N-(2-fluoro-2-methylpropyl)-10-[[6-(2-methyltetrazol-5-yl)pyridin-3-yl]amino]-7,8,9,10-tetrahydrobenzo[h]isoquinoline-5-sulfonamide Synthesised in the same manner as Example 6 using intermediate 12 (30 mg, 0.08 mmol) and comparable stoichiometries of reagents. Purification by column chromatography eluting with 0-20% MeOH in EtOAc followed by reverse phase column chromatography (basic conditions) gave the title compound (6 mg, 14% Yield). $\delta_H$ (300 MHz, d6-DMSO) 9.09 (s, 1H), 8.43 (s, 1H), 8.24 (d, J=2.7 Hz, 1H), 7.99 (s, 1H), 7.93 (d, J=8.6 Hz, 1H), 7.36 (dd, J=8.7, 2.8 Hz, 1H), 7.02 (d, J=8.4 Hz, 1H), 5.55 (s, 1H), 4.40 (s, 3H), 2.92 (dd, J=19.6, 9.9 Hz, 4H), 2.25-2.07 (m, 2H), 1.94 (s, 1H), 1.80 (d, J=14.2 Hz, 2H), 1.24 (d, J=21.4 Hz, 6H), 0.97 (d, J=8.2 Hz, 4H) [one H not visible]. LCMS $[M-H]^-$ 549, RT 1.18 min (Method 6).

Example 9

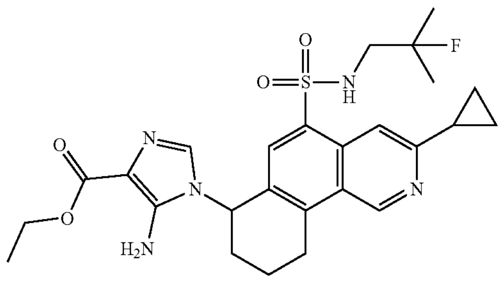 [SMILES: CCOC(=O)c1ncn(C2CCCc3c2cc(S(=O)(=O)NCC(C)(C)F)c2cc(C4CC4)ncc32)c1N]

ethyl 5-amino-1-[3-cyclopropyl-5-[(2-fluoro-2-methylpropyl)sulfamoyl]-7,8,9,10-tetrahydrobenzo[h]isoquinolin-7-yl]imidazole-4-carboxylate To a solution of ethyl 2-amino-2-cyanoacetate (15 mg, 0.07 mmol, 64% purity) in MeCN (1 mL) was added triethyl orthoformate (13 μL, 0.08 mmol). The resultant solution was heated at 90° C. for 1 hour then cooled to room temperature. Intermediate 10 (20 mg, 0.05 mmol) was then added and after 1 hour, the reaction mixture was conc. in vacuo and purified by reverse phase column chromatography (acidic conditions) to give the title compound (9 mg, 31% Yield). $\delta_H$ (300 MHz, d6-DMSO) 9.50 (s, 1H), 8.40 (s, 1H), 8.34 (d, J=0.8 Hz, 1H), 7.65 (s, 1H), 6.78 (s, 1H), 6.24-6.09 (m, 2H), 5.61 (t, J=6.1 Hz, 1H), 4.18 (q, J=7.1 Hz, 2H), 3.39 (d, J=16.4 Hz, 2H), 2.81 (dt, J=20.0, 6.7 Hz, 2H), 2.35-2.28 (m, 1H), 2.19-2.03 (m, 2H), 1.92 (d, J=10.2 Hz, 2H), 1.25 (t, J=7.1 Hz, 3H), 1.16 (d, J=21.4 Hz, 6H), 1.07 (d, J=6.9 Hz, 4H). LCMS $[M+H]^+$ 530, RT 1.68 min (Method 7).

Example 10

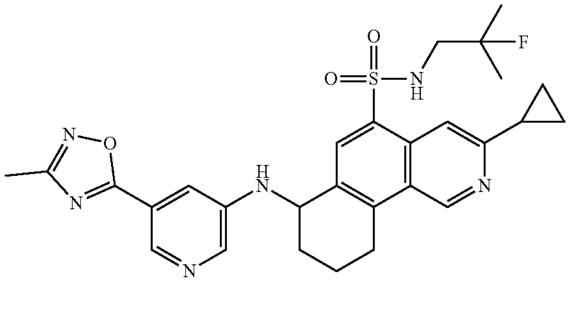 [SMILES: Cc1noc(-c2cncc(NC3CCCc4c3cc(S(=O)(=O)NCC(C)(C)F)c3cc(C5CC5)ncc43)c2)n1]

3-cyclopropyl-N-(2-fluoro-2-methylpropyl)-7-[[5-(3-methyl-1,2,4-oxadiazol-5-yl)pyridin-3-yl]amino]-7,8,9,10-tetrahydrobenzo[h]isoquinoline-5-sulfonamide Synthesised in the same manner as example 6 using intermediate 10 (25 mg, 0.06 mmol) and comparable stoichiometries of reagents and heating at 100° C. for 6 hours. Purification by column chromatography gave the title compound (3 mg, 8% Yield). $\delta_H$ (300 MHz, d6-DMSO) 9.49 (s, 1H), 8.54 (s, 1H), 8.47 (d, J=1.8 Hz, 1H), 8.37 (d, J=2.8 Hz, 2H), 8.16 (s, 1H), 7.69 (t, J=2.3 Hz, 1H), 6.92 (d, J=8.8 Hz, 1H), 5.02 (s, 1H), 3.43 (d, J=18.9 Hz, 2H), 2.86 (d, J=17.8 Hz, 2H), 2.43 (s, 3H), 2.32 (d, J=6.4 Hz, 1H), 1.97 (s, 4H), 1.20 (dd, J=21.4, 5.5 Hz, 6H), 1.07 (d, J=6.3 Hz, 4H). LCMS $[M+H]^+$ 551, RT 2.31 min (Method 8).

Example 11

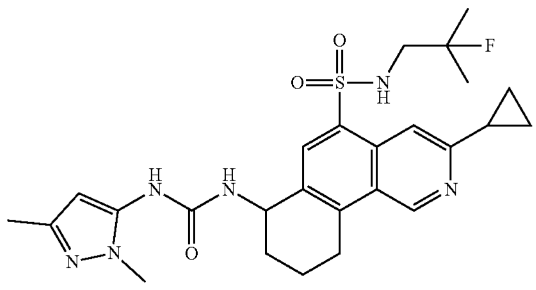 [SMILES: Cc1cc(NC(=O)NC2CCCc3c2cc(S(=O)(=O)NCC(C)(C)F)c2cc(C4CC4)ncc32)n(C)n1]

1-[3-cyclopropyl-5-[(2-fluoro-2-methylpropyl)sulfamoyl]-7,8,9,10-tetrahydrobenzo[h]isoquinolin-7-yl]-3-(2,5-dimethylpyrazol-3-yl) urea To a stirred solution of 1,3-dimethyl-1H-pyrazol-5-amine (8 mg, 0.07 mmol) in MeCN (1 mL) were added TEA (20 μL, 0.14 mmol) and 1,1'-carbonyldiimidazole (11 mg, 0.07 mmol). After 1 hour, intermediate 10 (25 mg, 0.07 mmol) was added. After a further 12 hours, the reaction mixture was diluted with brine (20 mL) and extracted with DCM (3×20 mL), the combined organics dried and conc. in vacuo. Purification by column chromatography eluting with 0-30% MeOH in EtOAc followed by reverse phase column chromatography (acidic conditions) gave the title compound (3 mg, 9% Yield). $\delta_H$ (300 MHz, d6-DMSO) 9.44 (s, 1H), 8.38 (s, 1H), 8.33 (d, J=7.6 Hz, 2H), 8.18 (s, 1H), 6.98 (d, J=8.6 Hz, 1H), 5.93 (s, 1H), 5.01 (s, 1H), 3.54 (s, 3H), 3.26 (s, 2H), 2.92 (d, J=18.9 Hz, 2H), 2.31 (d, J=6.5 Hz, 1H), 2.07 (s, 3H), 1.98 (s, 4H), 1.21 (dd, J=21.4, 6.8 Hz, 6H), 1.06 (d, J=6.8 Hz, 4H). LCMS $[M+H]^+$ 529, RT 1.88 min (Method 8).

Example 12

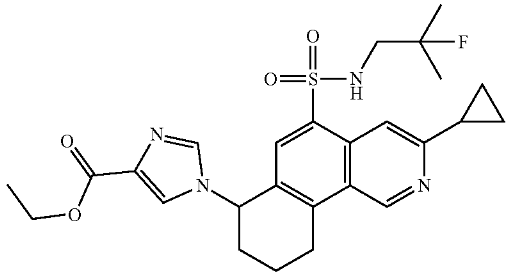 [SMILES: CCOC(=O)c1cn(C2CCCc3c2cc(S(=O)(=O)NCC(C)(C)F)c2cc(C4CC4)ncc32)cn1]

ethyl 1-[3-cyclopropyl-5[(2-fluoro-2-methylpropyl)sulfamoyl]-7,8,9,10-tetrahydrobenzo[h]isoquinolin-7-yl]imidazole-4-carboxylate To a stirred solution of ethyl (Z)-3-(dimethylamino)-2-isocyano-prop-2-enoate * (10 mg, 0.06 mmol) in 1-butanol (1 mL) was added intermediate 10 (20 mg, 0.05 mmol) and the resultant mixture heated at 150° C. for 9 hours. The mixture was then conc. in vacuo and purified by column chromatography eluting with 0-20% MeOH in EtOAc followed by reverse phase column chromatography eluting (basic conditions) to give the title compound (4 mg, 15% Yield). $\delta_H$ (400 MHz, d6-DMSO) 9.51 (s, 1H), 8.38 (s, 1H), 8.34 (s, 1H), 7.85 (d, J=1.3 Hz, 1H), 7.79 (d, J=1.3 Hz, 1H), 7.60 (s, 1H), 5.83 (t, J=6.3 Hz, 1H), 4.17 (qd, J=7.1, 2.0 Hz, 2H), 3.45-3.39 (m, 1H), 3.39-3.35 (m, 1H), 2.88-2.69 (m, 2H), 2.31-2.23 (m, 2H), 2.22-2.11 (m, 1H), 1.95 (s, 2H), 1.22 (t, J=7.0 Hz, 3H), 1.13 (dd, J=21.3, 2.4 Hz, 6H), 1.09-1.04 (m, 4H). LCMS $[M+H]^+$ 515, RT 2.03 min (Method 8).

* Synthesised according to the procedure in WO2007/42545 A1, 2007.

In Vitro Biochemical Assay

Protocol for Preparation of IgE-Tb Reagent 86 nmoles of IgE-Fc(N265Q, N371Q) (Young et al., 1995) at 172 μM in 100 mM $NaHCO_3$, pH 9.5 was added to 1 mg of LanthaScreen™ Amine Reactive Tb Chelate (ThermoFisher catalogue number PV3583) and incubated for 16 hours at 20° C. The material was then buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Tb conjugation determined by measuring the absorption at 280 nm and 343 nm.

The integrity of the conjugated material was determined by analytical size exclusion chromatography on a S200 HR 10×300 column (GE Healthcare). Typical conjugation ratios were 4:1 Tb:IgE-Fc.

Young R J., Owens, R J., MacKay G A., Chan C M W., Shi J., Hide M., Francis D M., Henry A J., Sutton B J, and Gould H J (1995) Protein Engineering 8:193-199

Protocol for Preparation of sFcεR1α-Y131A-AF488 Reagent 400 nmoles FcεR1α(Y131A mutant) (Cook et al., 1997) at 400 μM in 100 mM NaOAc pH 5.5 was reacted with 1 mM final concentration sodium periodate (in 100 mM NaOAc, pH 5.5) for 60 minutes at 22° C. Oxidation was quenched with the addition of 40 μL of ethanediol and incubation for 60 minutes at 22° C. The protein was buffer exchanged in to conjugation buffer (50 mM $NaHCO_3$, 150 mM NaCl, pH 9.5) and concentrated to 750 μM.

175 nmoles of protein was added to 1 mg of Alexa Fluor™ 488 hydrazide (Invitrogen) and incubated for 16 hours at 22° C. Sodium cyanoborohydride (at 100 mM in conjugation buffer) was added to a final concentration of 1 mM and incubated for 60 minutes on ice. The protein was buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Alexa Fluor™ 488 conjugation determined by measuring the absorption at 280 nm and 495 nm.

The integrity of the conjugated material was determined by analytical size exclusion chromatography on a S200 HR 10×300 column (GE Healthcare). Typical conjugation ratios were 2:1 Alexa Fluor™488: sFcεR1α

Cook J P D., Henry A J, McDonnell J M., Owens R J., Sutton B J., and Gould H J (1997) Biochemistry 36:15579-15588

The aim was to measure binding of IgE-Tb to receptor, and the inhibition thereof by compounds, using an in vitro Fluorescence Resonance Energy Transfer (FRET) Assay.

Reagents

FRET reagents used were IgE labelled with Terbium (FRET donor), and soluble IgE receptor FcεRIα with a Y131A mutation, labelled with Alexa Fluor™ 488 (FRET acceptor). Unlabelled FcεRIα was also used to generate a background control. The assay buffer consisted of 20 mM Tris pH7.2, 150 mM NaCl, and 0.002% Tween, 1% DMSO.

Assay Reaction

The assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by IgE-Tb diluting 10-fold in assay buffer. For the assay, 5 μl of diluted compound was added to 10 μl of, followed by addition of 10 μl FcεRIα-Y131A-AF488. FRET reagents FACs were 5 nM IgE-Tb, 25 nM FcεRIα-Y131A-AF488. Usually the top FAC of compound in the assay was 10 μM. The final DMSO concentration was 2%. The minimum signal (MIN) was measured by adding 5 μl unlabelled FcεRIα at 1 μM (FAC=200 nM) to the FRET reagents. The maximum FRET signal (MAX) was measured in wells containing FRET reagents but no compound.

The assay was incubated for 2 hours at room temperature, protected from light and evaporation, and with gentle agitation.

FRET Measurement

Measurement of FRET for each well was carried out by exciting at 330 nm and measuring emission at 495/520 nm using an Envision plate reader (Perkin Elmer). FRET ratio was calculated as follows:

Emission at 520/Emission at 495×1000.

The FRET ratio was used for the data analysis.

Data Analysis

Z' was calculated as follows (σ=standard deviation and μ=mean):

$$1-((3\times\sigma^{MAX})+(3\times\sigma_{MIN}))/(\mu_{MAX}-\mu_{MIN})$$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Percent inhibition was plotted against compound concentration. IC50 values for each compound were determined using four parameter logistic fit model using the XLFIT5 software package.

The results are as follows:

Compounds of the invention show an IC50 value ranging from 19.8 nM to 5098 nM.

The table below shows the range of IC50 values for each example:

| Example Number | FRET $IC_{50}$ range |
| --- | --- |
| 6 | 10-50 nanomolar |
| 2, 10 | 50-100 nanomolar |
| 1, 3, 4, 7, 8, 9, 11, 12 | 0.1-1 micromolar |
| 5 | 1-5 micromolar |

The invention claimed is:

1. A compound of formula (I) or a pharmaceutically acceptable salt thereof:

(I)

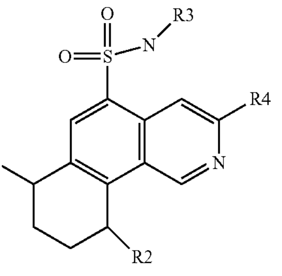

wherein

R1 and R2 independently represent:

Hydrogen; or NHC(O)NH—C1-6-alkyl; or $NHSO_2$—C1-6-alkyl; or NHC(O)NH-heteroaryl optionally substituted with one or more $R1_a$; or heteroaryl optionally substituted with one or more group selected from the group consisting of amino; C1-6-alkyl; C(O)O—C1-6-alkyl; nitrile; heteroaryl optionally substituted with one or more $R1_a$; NH—C1-6-alkyl; NH—C1-6-heterocycloalkyl; NH—C3-9-cycloalkyl; NH-heteroaryl optionally substituted with one or more $R1_a$; or NH-heteroaryl optionally substituted with one or more group selected from the group consisting of C1-6-alkyl; C1-6-hydroxyalkyl; C3-9-hydroxyheterocycloalkyl; heteroaryl optionally substituted with one or more $R1_a$; or NHC(O)—C1-6-alkyl; or NHC(O)-heteroaryl optionally substituted with one or more $R1_a$ $R1_a$ represents a group selected from the group consisting of:

Halogen; nitrile; C1-6-alkyl; C1-6-haloalkyl; C1-6-alkoxy; C1-6-haloalkoxy; C(O)O—C1-6-alkyl; and C(O) OH;

R3 represents a group selected from the group consisting of:

C1-6-alkyl optionally substituted with one or more $R3^a$ groups;

C1-3-alkanediyl-C3-6-cycloalkyl optionally substituted with one or more $R3^a$ groups;

C1-3-alkanediyl-C3-6-heterocycloalkyl optionally substituted with one or more $R3^a$ groups;

C3-6-heterocycloalkyl optionally substituted with one or more $R3^a$ groups; and C3-6-cycloalkyl optionally substituted with one or more $R3^a$ groups;

$R3^a$ represents a group selected from the group consisting of hydrogen; Halogen; C1-2-alkyl; hydroxy; and C1-2-alkoxy; and R4 represents:

C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group;

$R4^a$ represents a group selected from the group consisting of hydroxy; Halogen;

and C1-2-alkyl.

2. A compound according to claim 1, wherein

R1 and R2 independently represent:

Hydrogen; or NH-heteroaryl optionally substituted with one or more group selected from the group consisting of C1-6-alkyl; heteroaryl optionally substituted with one or more $R1_a$; or heteroaryl optionally substituted with one or more group selected from the group consisting of amino; C(O)O—C1-6-alkyl; nitrile; heteroaryl optionally substituted with one or more $R1_a$; NH—C1-6-alkyl; NH—C3-9-heterocycloalkyl; NH—C3-9-cycloalkyl; or NH-heteroaryl optionally substituted with one or more $R1_a$.

3. A compound according to claim 2, wherein

When R1 is different than hydrogen, R2 is hydrogen;

When R2 is different than hydrogen, R1 is hydrogen.

4. A compound according to claim 2, wherein

R3 represents C1-6-alkyl optionally substituted with a fluorine atom.

5. A compound according to claim 2, wherein

R4 represents cyclopropyl.

6. A compound according to claim 1, wherein

When R1 is different than hydrogen, R2 is hydrogen; or

When R2 is different than hydrogen, R1 is hydrogen.

7. A compound according to claim 6, wherein

R3 represents C1-6-alkyl optionally substituted with a fluorine atom.

8. A compound according to claim 6, wherein

R4 represents cyclopropyl.

9. A compound according to claim 1, wherein

R3 represents C1-6-alkyl optionally substituted with a fluorine atom.

10. A compound according to claim 9, wherein

R4 represents cyclopropyl.

11. A compound according to claim 1, wherein

R4 represents cyclopropyl.

12. A compound according to claim 1 which is:

3-cyclopropyl-N-(2-methylpropyl)-7,8,9,10-tetrahydrobenzo[h]isoquinoline-5-sulfonamide;

1-[3-cyclopropyl-5-(2-methylpropylsulfamoyl)-7,8,9,10-tetrahydrobenzo[h]isoquinolin-7-yl]-3-ethylurea;

1-[3-cyclopropyl-5-(2-methylpropylsulfamoyl)-7,8,9,10-tetrahydrobenzo[h]isoquinolin-10-yl]-3-ethylurea;

3-cyclopropyl-7-(methanesulfonamido)-N-(2-methylpropyl)-7,8,9,10-tetrahydrobenzo[h]isoquinoline-5-sulfonamide;

3-cyclopropyl-10-(methanesulfonamido)-N-(2-methylpropyl)-7,8,9,10-tetrahydrobenzo[h]isoquinoline-5-sulfonamide;

3-cyclopropyl-N-(2-fluoro-2-methylpropyl)-7-[[6-(2-methyltetrazol-5-yl) pyridin-3-yl]amino]-7,8,9,10-tetrahydrobenzo[h]isoquinoline-5-sulfonamide;

3-cyclopropyl-7-[3-[(2,5-dimethylpyrazol-3-yl)amino]-1,2,4-triazol-4-yl]-N-(2-fluoro-2-methylpropyl)-7,8,9,10-tetrahydrobenzo[h]isoquinoline-5-sulfonamide;

3-cyclopropyl-N-(2-fluoro-2-methylpropyl)-10-[[6-(2-methyltetrazol-5-yl) pyridin-3-yl]amino]-7,8,9,10-tetrahydrobenzo[h]isoquinoline-5-sulfonamide;

ethyl 5-amino-1-[3-cyclopropyl-5-[(2-fluoro-2-methylpropyl) sulfamoyl]-7,8,9,10-tetrahydrobenzo[h]isoquinolin-7-yl]imidazole-4-carboxylate;

3-cyclopropyl-N-(2-fluoro-2-methylpropyl)-7-[[5-(3-methyl-1,2,4-oxadiazol-5-yl) pyridin-3-yl]amino]-7,8,9,10-tetrahydrobenzo[h]isoquinoline-5-sulfonamide;

1-[3-cyclopropyl-5-[(2-fluoro-2-methylpropyl) sulfamoyl]-7,8,9,10-tetrahydrobenzo[h]isoquinolin-7-yl]-3-(2,5-dimethylpyrazol-3-yl) urea; or ethyl 1-[3-cyclopropyl-5-[(2-fluoro-2-methylpropyl) sulfamoyl]-7,8,9,10-tetrahydrobenzo[h]isoquinolin-7-yl] imidazole-4-carboxylate.

13. A method for the treatment or prevention of allergy, non-allergic mast cell responses, type 1 hypersensitivity, urticaria, or familiar sinus inflammation comprising administration to a patient in need thereof a compound according to claim 1 or a pharmaceutically acceptable salt thereof.

14. A method for the treatment or prevention of airway constriction in asthma, local inflammation in eczema, increased mucus secretion in allergic rhinitis, urticaria, or increased vascular permeability comprising administration to a patient in need thereof a compound according to claim 1 or a pharmaceutically acceptable salt thereof.

15. A pharmaceutical composition comprising a compound of formula (I) according to claim 1 or a pharmaceutically acceptable salt thereof and a pharmaceutically acceptable carrier.

* * * * *